(12) United States Patent
Madrid et al.

(10) Patent No.: US 6,689,157 B2
(45) Date of Patent: *Feb. 10, 2004

(54) DUAL WIRE PLACEMENT CATHETER

(75) Inventors: Gilbert Madrid, Laguna Niguel, CA (US); Myles Douglas, Phoenix, AZ (US); Samuel M. Shaolian, Newport Beach, CA (US)

(73) Assignee: Endologix, Inc., Irvine, CA (US)

( * ) Notice: Subject to any disclaimer, the term of this patent is extended or adjusted under 35 U.S.C. 154(b) by 29 days.

This patent is subject to a terminal disclaimer.

(21) Appl. No.: 10/035,729

(22) Filed: Dec. 21, 2001

(65) Prior Publication Data

US 2002/0058905 A1 May 16, 2002

Related U.S. Application Data

(63) Continuation of application No. 09/348,356, filed on Jul. 7, 1999, now Pat. No. 6,440,161.

(51) Int. Cl.⁷ .................................. A61F 2/06
(52) U.S. Cl. ............... 623/1.11; 623/1.35; 606/108
(58) Field of Search ................ 604/96.01, 500, 604/506–510, 264, 523, 528, 164.01, 164.13; 623/1.11, 1.12, 1.35, 1.16, 66.1, 1.2; 606/153, 191, 108, 192, 194, 198

(56) References Cited

U.S. PATENT DOCUMENTS

| | | |
|---|---|---|
| 2,437,542 A | 3/1948 | Krippendorf |
| 4,617,932 A | 10/1986 | Kornberg |
| 4,878,906 A | 11/1989 | Lindemann et al. |
| 4,922,905 A | 5/1990 | Strecker |
| 4,994,071 A | 2/1991 | Macgregor |
| 5,019,090 A | 5/1991 | Pinchuk |
| 5,078,726 A | 1/1992 | Kreamer |
| 5,123,917 A | 6/1992 | Lee |

(List continued on next page.)

FOREIGN PATENT DOCUMENTS

| | | |
|---|---|---|
| EP | 0 775 470 A1 | 5/1997 |
| EP | 0 904 745 A2 | 3/1999 |
| WO | WO 97/26936 | 1/1997 |
| WO | WO 99/44536 | 9/1999 |
| WO | WO 99/47077 | 9/1999 |

OTHER PUBLICATIONS

US 5,690,647, 11/1997, Osborne (withdrawn)

*Primary Examiner*—Glenn K. Dawson
*Assistant Examiner*—Jennifer J Maynard
(74) *Attorney, Agent, or Firm*—Knobbe, Martens, Olson & Bear, LLP

(57) ABSTRACT

Disclosed is a dual lumen access catheter, for facilitating placement of two procedure wires across a treatment site. In one application, the catheter is used to place a first wire extending between a contralateral iliac and an ipsilateral iliac across the terminal bifurcation of the aorta, and a second wire extending through a portion of the ipsilateral iliac and into the aorta. Methods of placing the wires, such as for subsequent deployment of an abdominal aortic aneurysm bifurcation graft, are also disclosed.

27 Claims, 13 Drawing Sheets

U.S. PATENT DOCUMENTS

| | | |
|---|---|---|
| 5,195,978 A | 3/1993 | Schiffer |
| 5,197,976 A | 3/1993 | Herweck et al. |
| 5,201,757 A | 4/1993 | Heyn et al. |
| 5,256,141 A | 10/1993 | Gendheff et al. |
| 5,263,932 A | 11/1993 | Jang |
| 5,275,622 A | 1/1994 | Lazarus et al. |
| 5,316,023 A | 5/1994 | Palmaz et al. |
| 5,320,602 A | 6/1994 | Karpiel |
| 5,342,387 A | 8/1994 | Summers |
| 5,354,308 A | 10/1994 | Simon et al. |
| 5,360,443 A | 11/1994 | Barone et al. |
| 5,370,683 A | 12/1994 | Fontaine |
| 5,387,235 A | 2/1995 | Chuter |
| 5,456,713 A | 10/1995 | Chuter |
| 5,462,530 A | 10/1995 | Jang |
| 5,489,295 A | 2/1996 | Piplani et al. |
| 5,507,769 A | 4/1996 | Marin et al. |
| 5,507,771 A | 4/1996 | Gianturco |
| 5,554,118 A | 9/1996 | Jang |
| 5,562,728 A | 10/1996 | Lazarus et al. |
| 5,571,173 A | 11/1996 | Parodi |
| 5,575,818 A | 11/1996 | Pinchuk |
| 5,578,072 A | 11/1996 | Barone et al. |
| 5,609,627 A | 3/1997 | Goicoechea et al. |
| 5,628,788 A | 5/1997 | Pinchuk |
| 5,632,772 A | 5/1997 | Alcime et al. |
| 5,639,278 A | 6/1997 | Dereume et al. |
| 5,653,743 A | 8/1997 | Martin |
| 5,662,614 A | 9/1997 | Edoga |
| 5,662,703 A | 9/1997 | Yurek et al. |
| 5,665,115 A | 9/1997 | Cragg |
| 5,669,880 A | 9/1997 | Solar |
| 5,669,924 A | 9/1997 | Shaknovich |
| 5,676,696 A | 10/1997 | Marcade |
| 5,676,697 A | 10/1997 | McDonald |
| 5,683,450 A | 11/1997 | Goicoechea et al. |
| 5,683,451 A | 11/1997 | Lenker et al. |
| 5,683,452 A | 11/1997 | Barone et al. |
| 5,683,453 A | 11/1997 | Palmaz |
| 5,690,644 A | 11/1997 | Yurek et al. |
| 5,693,084 A | 12/1997 | Chuter |
| 5,693,088 A | 12/1997 | Lazarus |
| 5,695,517 A | 12/1997 | Marin et al. |
| 5,720,735 A | 2/1998 | Dorros |
| 5,720,776 A | 2/1998 | Chuter et al. |
| 5,723,004 A | 3/1998 | Dereume et al. |
| 5,746,766 A | 5/1998 | Edoga |
| 5,749,880 A | 5/1998 | Banas et al. |
| 5,769,885 A | 6/1998 | Quiachon et al. |
| 5,800,508 A | 9/1998 | Goicoechea et al. |
| 5,824,039 A | 10/1998 | Piplani et al. |
| 5,851,228 A | 12/1998 | Pinheiro |
| 5,879,321 A | 3/1999 | Hill |
| 5,928,279 A | 7/1999 | Shannon et al. |
| 6,039,749 A | 3/2000 | Marin et al. |
| 6,039,755 A | 3/2000 | Edwin et al. |
| 6,039,758 A | 3/2000 | Quiachon et al. |
| 6,051,020 A | 4/2000 | Goicoechea et al. |
| 6,070,589 A * | 6/2000 | Keith et al. ................. 128/898 |
| 6,074,398 A | 6/2000 | Leschinsky |
| 6,077,297 A | 6/2000 | Robinson et al. |
| 6,117,167 A | 9/2000 | Goicoechea et al. |
| 6,123,722 A | 9/2000 | Fogarty et al. |
| 6,123,723 A | 9/2000 | Konya et al. |
| 6,126,685 A | 10/2000 | Lenker et al. |
| 6,129,756 A | 10/2000 | Kugler et al. |
| 6,168,610 B1 | 1/2001 | Marin et al. |
| 6,192,944 B1 | 2/2001 | Greenhalgh |
| 6,350,278 B1 | 2/2002 | Lenker et al. |
| 6,440,161 B1 * | 8/2002 | Madrid et al. ............. 623/1.11 |
| 6,582,390 B1 | 6/2003 | Sanderson |
| 2002/0049412 A1 | 4/2002 | Madrid et al. |

* cited by examiner

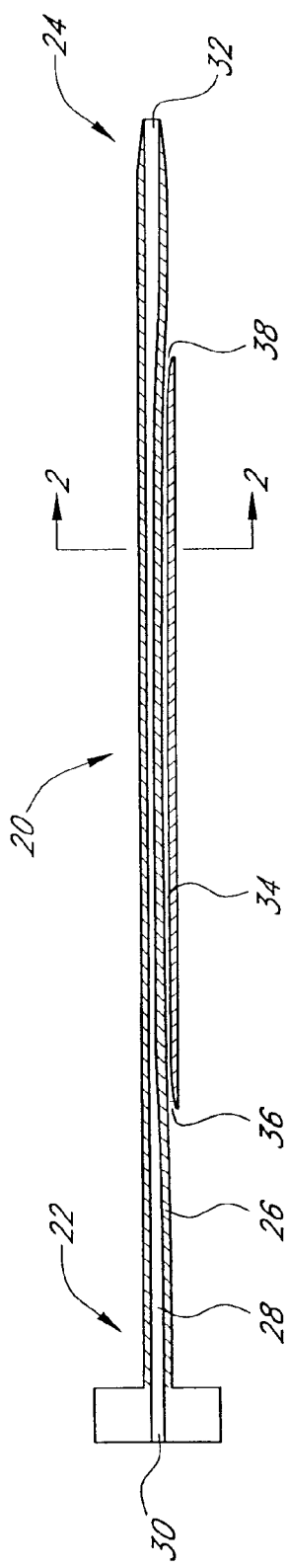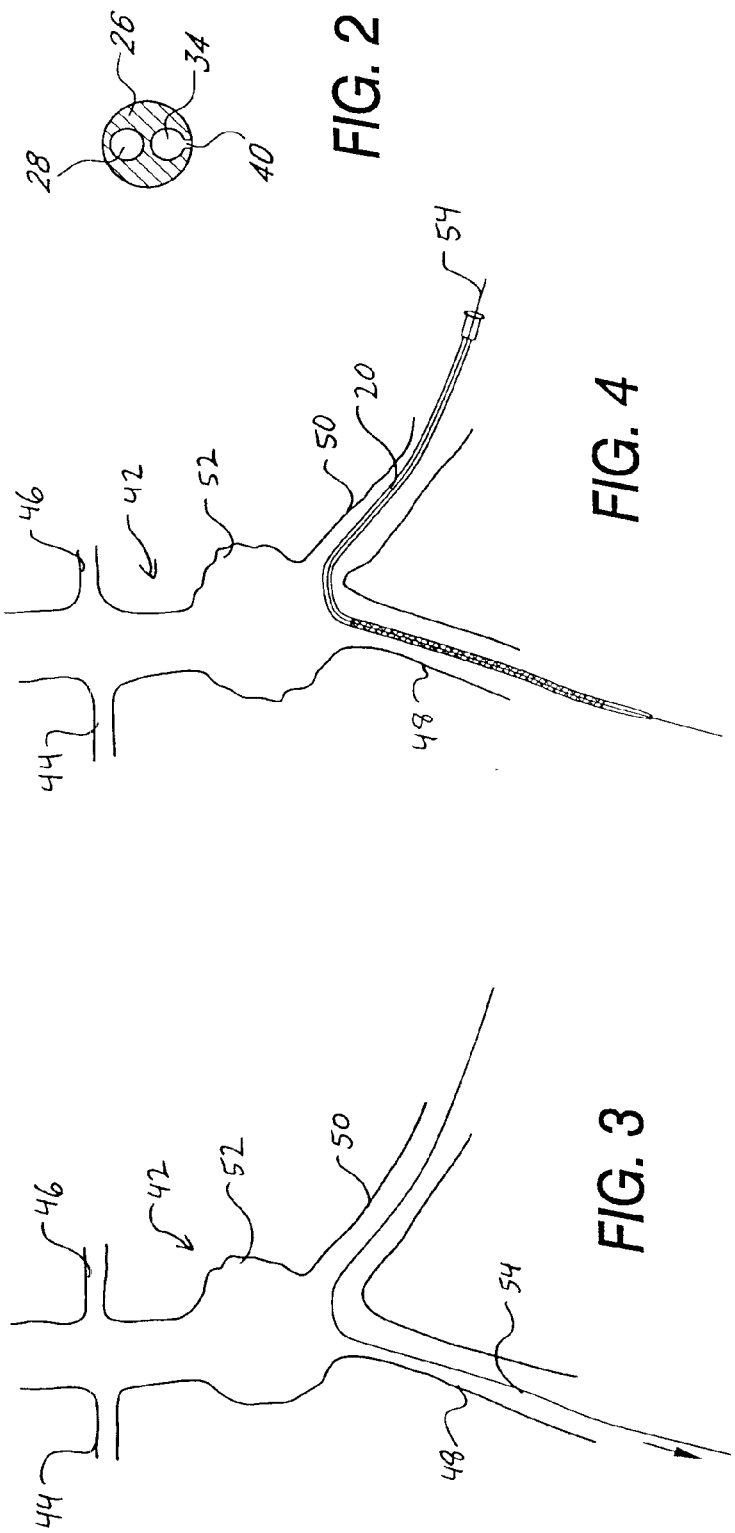

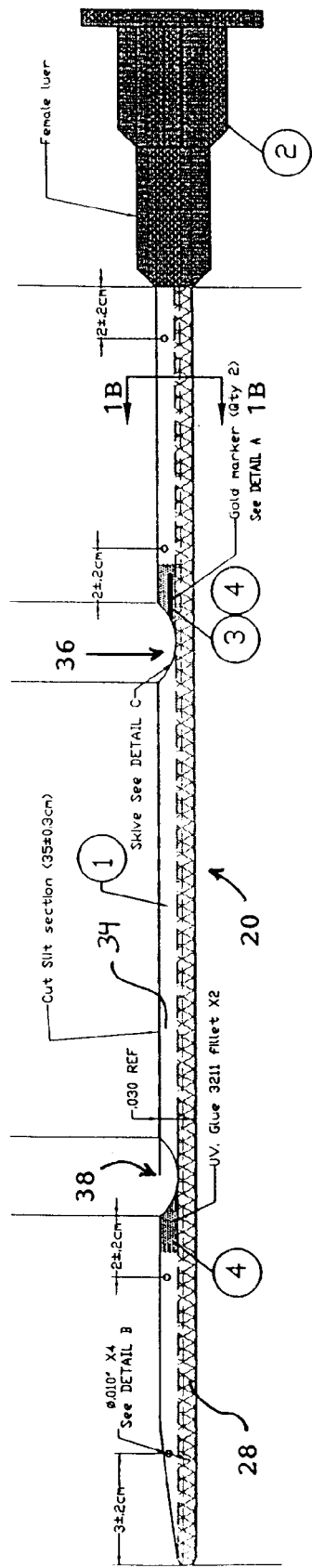
FIGURE 1A

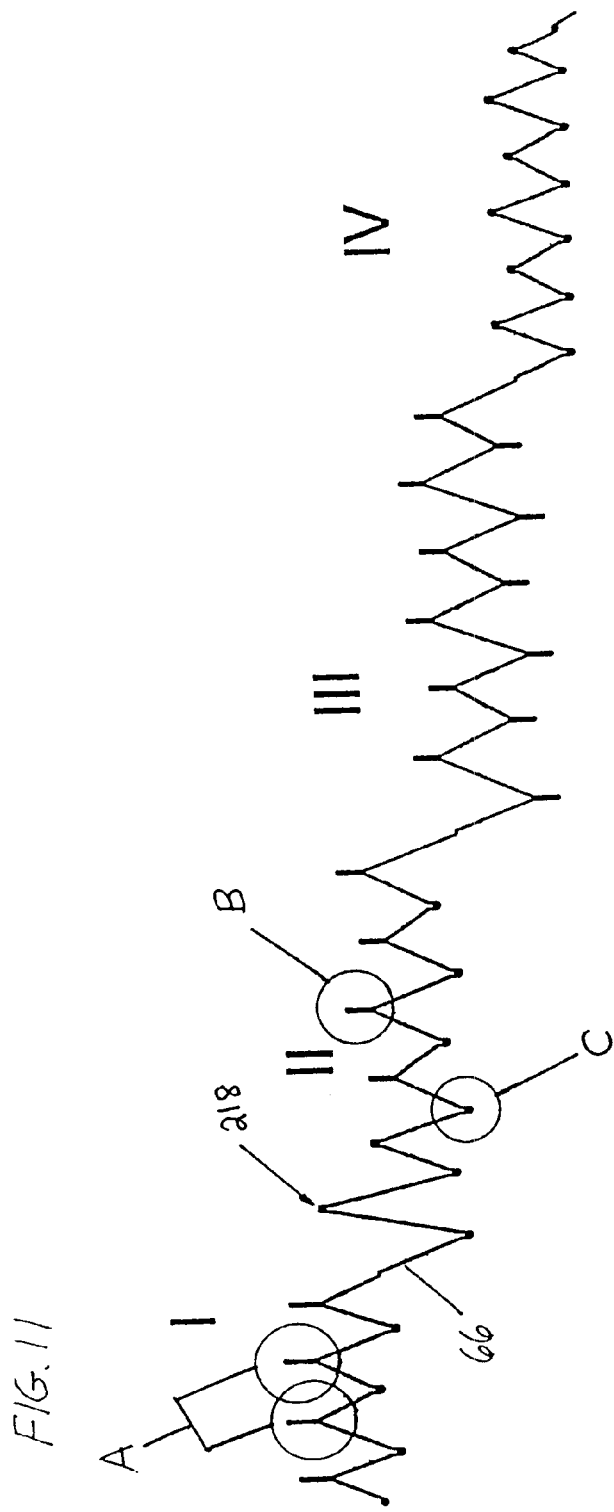
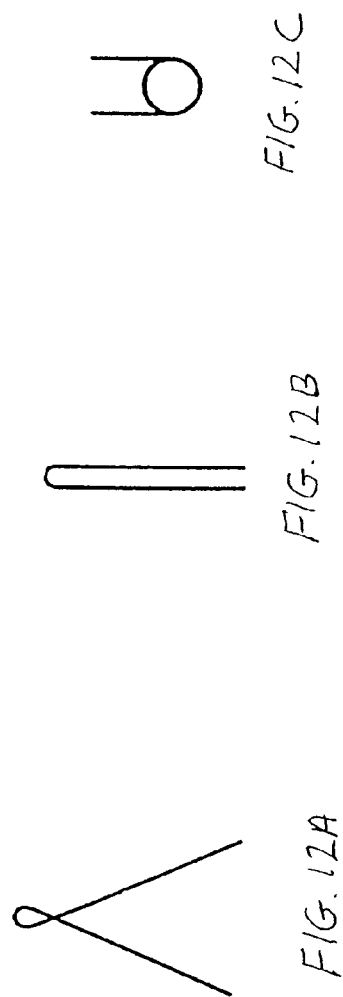

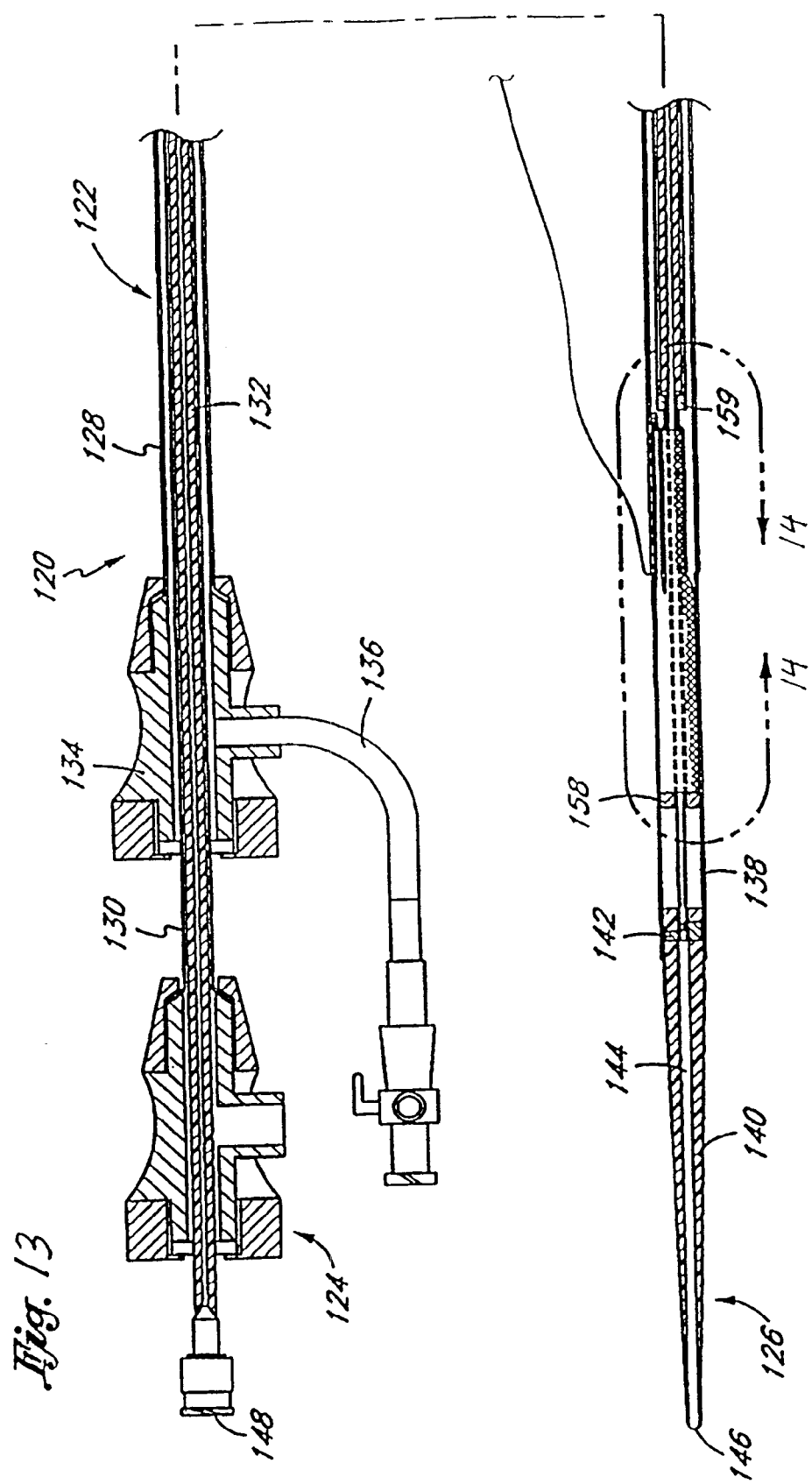

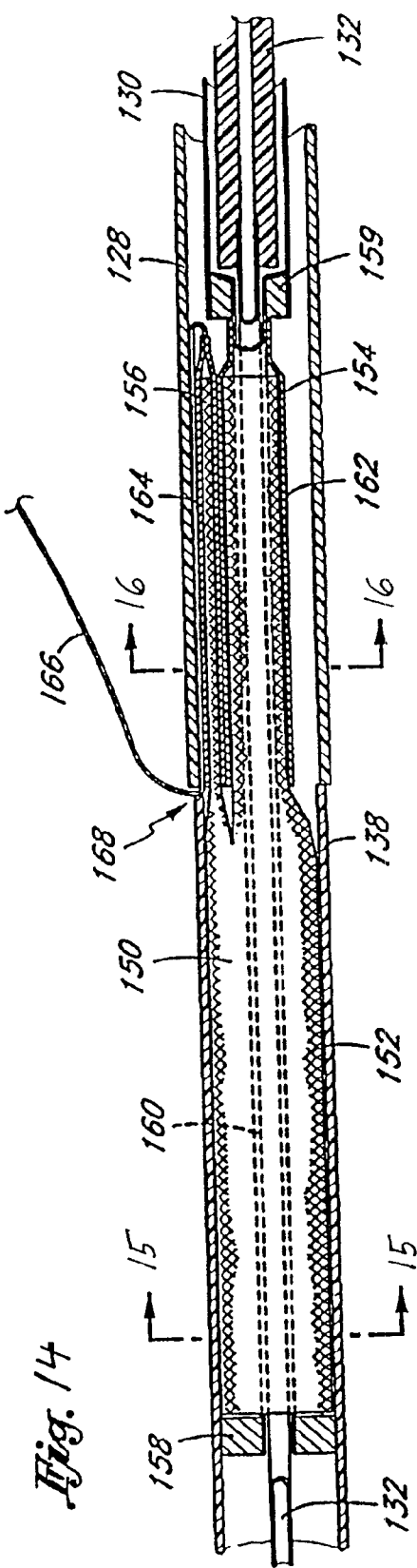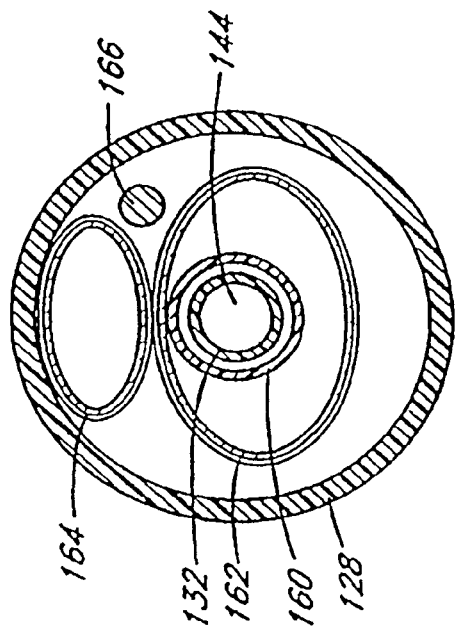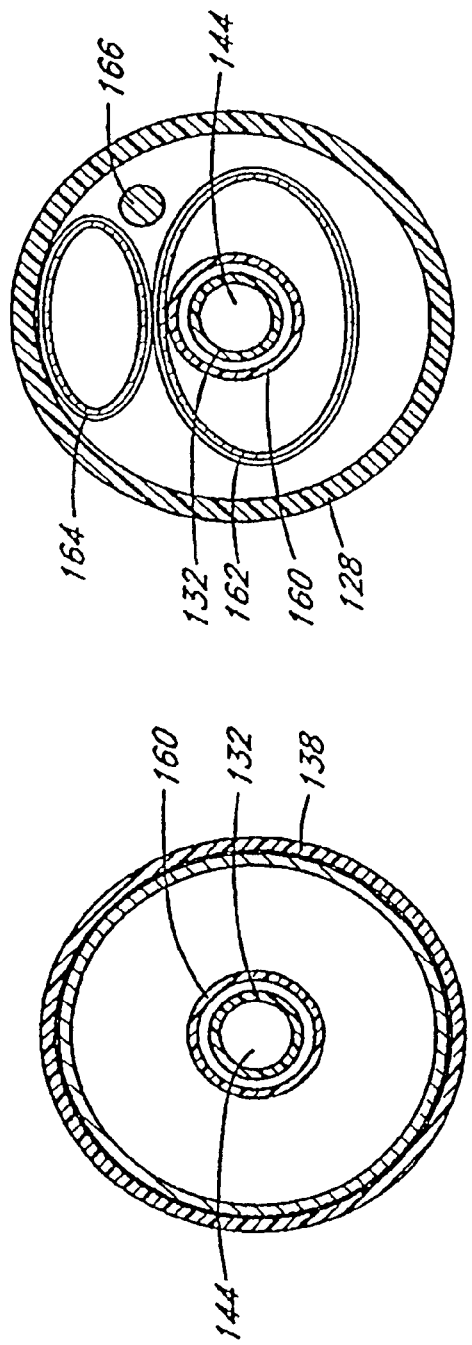

DUAL WIRE PLACEMENT CATHETER

PRIORITY INFORMATION

The present application is a continuation application of U.S. patent application Ser. No. 09/348,356 filed Jul. 7, 1999, now issued as U.S. Pat. No. 6,440,161; this application claims priority to the early filed application under 35 U.S.C. §120.

BACKGROUND OF THE INVENTION

The present invention relates to catheters, and, in particular, to a dual lumen catheter for use in positioning two wires in a vascular bifurcation such as in connection with the treatment of abdominal aortic aneurysms.

An abdominal aortic aneurysm is a sac caused by an abnormal dilation of the wall of the aorta, a major artery of the body, as it passes through the abdomen. The abdomen is that portion of the body which lies between the thorax and the pelvis. It contains a cavity, known as the abdominal cavity, separated by the diaphragm from the thoracic cavity and lined with a serous membrane, the peritoneum. The aorta is the main trunk, or artery, from which the systemic arterial system proceeds. It arises from the left ventricle of the heart, passes upward, bends over and passes down through the thorax and through the abdomen to about the level of the fourth lumbar vertebra, where it divides into the two common iliac arteries.

The aneurysm usually arises in the infrarenal portion of the diseased aorta, for example, below the kidneys. When left untreated, the aneurysm may eventually cause rupture of the sac with ensuing fatal hemorrhaging in a very short time. High mortality associated with the rupture led initially to transabdominal surgical repair of abdominal aortic aneurysms. Surgery involving the abdominal wall, however, is a major undertaking with associated high risks. There is considerable mortality and morbidity associated with this magnitude of surgical intervention, which in essence involves replacing the diseased and aneurysmal segment of blood vessel with a prosthetic device which typically is a synthetic tube, or graft, usually fabricated of Polyester, Urethane, DACRON® TEFLON®, or other suitable material.

To perform the surgical procedure requires exposure of the aorta through an abdominal incision which can extend from the rib cage to the pubis. The aorta must be closed both above and below the aneurysm, so that the aneurysm can then be opened and the thrombus, or blood clot, and arteriosclerotic debris removed. Small arterial branches from the back wall of the aorta are tied off. The DACRON® tube, or graft, of approximately the same size of the normal aorta is sutured in place, thereby replacing the aneurysm. Blood flow is then reestablished through the graft. It is necessary to move the intestines in order to get to the back wall of the abdomen prior to clamping off the aorta.

If the surgery is performed prior to rupturing of the abdominal aortic aneurysm, the survival rate of treated patients is markedly higher than if the surgery is performed after the aneurysm ruptures, although the mortality rate is still quite high. If the surgery is performed prior to the aneurysm rupturing, the mortality rate is typically slightly less than 10%. Conventional surgery performed after the rupture of the aneurysm is significantly higher, one study reporting a mortality rate of 66.5%. Although abdominal aortic aneurysms can be detected from routine examinations, the patient does not experience any pain from the condition. Thus, if the patient is not receiving routine examinations, it is possible that the aneurysm will progress to the rupture stage, wherein the mortality rates are significantly higher.

Disadvantages associated with the conventional, prior art surgery, in addition to the high mortality rate include the extended recovery period associated with such surgery; difficulties in suturing the graft, or tube, to the aorta; the loss of the existing aorta wall and thrombosis to support and reinforce the graft; the unsuitability of the surgery for many patients having abdominal aortic aneurysms; and the problems associated with performing the surgery on an emergency basis after the aneurysm has ruptured. A patient can expect to spend from one to two weeks in the hospital after the surgery, a major portion of which is spent in the intensive care unit, and a convalescence period at home from two to three months, particularly if the patient has other illnesses such as heart, lung, liver, and/or kidney disease, in which case the hospital stay is also lengthened. The graft must be secured, or sutured, to the remaining portion of the aorta, which may be difficult to perform because of the thrombosis present on the remaining portion of the aorta. Moreover, the remaining portion of the aorta wall is frequently friable, or easily crumbled.

Since many patients having abdominal aortic aneurysms have other chronic illnesses, such as heart, lung, liver and/or kidney disease, coupled with the fact that many of these patients are older, the average age being approximately 67 years old, these patients are not ideal candidates for such major surgery.

More recently, a significantly less invasive clinical approach to aneurysm repair, known as endovascular grafting, has been developed. Parodi, et al. provide one of the first clinical descriptions of this therapy. Parodi, J. C., et al., "Transfemoral Intraluminal Graft Implantation for Abdominal Aortic Aneurysms," 5 Annals of Vascular Surgery 491 (1991). Endovascular grafting involves the transluminal placement of a prosthetic arterial graft within the lumen of the artery.

In general, transluminally implantable prostheses adapted for use in the abdominal aorta comprise a tubular wire cage surrounded by a tubular PTFE or Dacron sleeve. Both balloon expandable and self expandable support structures have been proposed. Endovascular grafts adapted to treat both straight segment and bifurcation aneurysms have also been proposed.

One persistent challenge in the context of implanting an endoluminal bifurcation graft relates to the proper positioning of the procedure wires across the deployment site. The most recent procedures and devices require a puncture or cut-down in both the right and left femoral arteries, and the time consuming step of placing a guidewire across the bifurcation between the contralateral and ipsilateral iliacs. A second wire must also be introduced into the ipsilateral iliac and advanced beyond the bifurcation into the aorta. Due to the two-dimensional viewing media currently available for such procedures, the clinician cannot visually tell if two guidewires are crossed or separated. As the advancement of two guidewires is made to separate sites, advancement of one guidewire may limit the advancement of the other if the wires become crossed.

Thus, notwithstanding the many advances which have been made in recent years in the treatment of abdominal aortic aneurysms, there remains a need for an improved method and device for more efficiently introducing a first contralateral-ipsilateral iliac wire and a second ipsilateral-aorta wire which may subsequently be used for positioning and/or deployment steps in a bifurcation graft deployment procedure.

SUMMARY OF THE INVENTION

There is provided in accordance with one aspect of the present invention, a multi-lumen catheter. The catheter comprises an elongate flexible tubular body, having a proximal end and a distal end. A first lumen extends throughout the length of the tubular body, between the proximal end and the distal end. A second lumen extends between a proximal port and a distal port, wherein the proximal port is spaced apart from the proximal end of the catheter and the distal port is spaced apart from the distal end of the catheter. The distal port is spaced proximally apart from the distal end of the catheter by at least about two centimeters, preferably at least about 10 cm and, in one embodiment, at least about 17 cm.

Preferably, the second lumen is defined by a wall which further comprises an axially extending tear line. The tear line may comprise a perforation line, and/or a reduced wall thickness. Alternatively, the second lumen is defined by a wall which further comprises an axially extending slit.

In accordance with another aspect of the present invention, there is provided a method of positioning a first wire through a portion of the ipsilateral iliac, across the bifurcation of the aorta and through at least a portion of the contralateral iliac. Additionally, a second wire is advanced through a portion of the ipsilateral iliac and into the aorta.

The method comprises the steps of introducing a catheter through a first access site into the contralateral iliac, the catheter having at least first and second lumens. The catheter is advanced superiorly to the bifurcation of the aorta and inferiorly down the ipsilateral iliac to a second access site. A first wire is introduced through the first lumen from the second access site through the first access site. A second wire is introduced through the second lumen from the second access site superiorly through the ipsilateral iliac, exiting a proximal port and into the aorta. The catheter is thereafter removed, while leaving the first and second wires in place.

Preferably, the removing step comprises tearing the wall of the second lumen, in response to proximal retraction of the catheter.

In one application of the invention, the method further comprises the step of introducing a bifurcation graft delivery catheter and advancing it along the second wire into the aorta. The first wire comprises a release wire for releasing the contralateral iliac branch of the bifurcation graft, from a constrained configuration to an expanded configuration within the contralateral iliac.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 1 is a side elevational schematic cross-section of a dual lumen catheter in accordance with the present invention.

FIG. 1A is a side elevational view of one embodiment of a dual lumen catheter in accordance with the present invention.

FIG. 1B is a cross section taken along the line 1B—1B in FIG. 1A.

FIG. 1C is a detailed view taken along the line 1C—1C in FIG. 1A.

FIG. 2 is a cross-section along the line 2—2 in FIG. 1.

FIG. 3 is a schematic representation of the bifurcation of the lower abdominal aorta into the ipsilateral and contralateral iliacs, with a standard guidewire inserted from the contralateral to the ipsilateral iliac.

FIG. 4 is a schematic representation as in FIG. 3, with the dual lumen catheter positioned over the guidewire.

FIG. 11 is a plan view of a formed wired useful for rolling about an axis to form a branch support structure in accordance with the embodiment shown in FIG. 9.

FIGS. 12A, 12B and 12C are enlargements of the apexes delineated by lines A, B and C respectively in FIG. 11.

FIG. 13 is a side elevational cross-section of a bifurcation graft delivery catheter useful for introducing a bifurcation graft along the guidewires placed by the dual lumen access catheter of the present invention.

FIG. 14 is an enlargement of the portion delineated by the line 14—14 in FIG. 13.

FIG. 15 is a cross-section taken along the line 15—15 in FIG. 14.

FIG. 16 is a cross-section taken along the line 16—16 in FIG. 14.

DETAILED DESCRIPTION OF THE PREFERRED EMBODIMENTS

Figure 6:
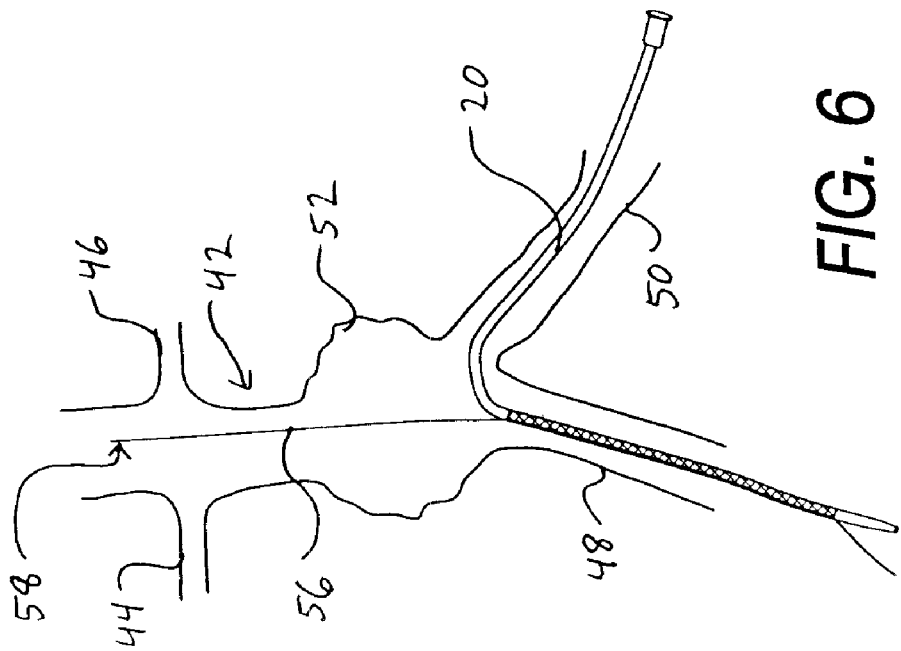
FIG. 6 is a schematic representation as in FIG. 5, after the delivery system guidewire has been advanced through the second wire lumen of the dual lumen catheter.

Referring to FIG. 1, there is illustrated a dual lumen catheter 20 in accordance with one aspect of the present invention. The dual lumen catheter 20 comprises a proximal end 22, a distal end 24 and an elongate flexible tubular body 26 extending therebetween.

In one application of the present invention the dual lumen catheter 20 is used to position wires for the purpose of transluminal introduction of an expandable graft at the bifurcation of the lower abdominal aorta and the ipsilateral and contralateral iliac arteries. In this application, the tubular body 26 has a length of within the range of from about 80 cm to about 100 cm and an outside diameter within the range of from about 0.105" to about 0.120". In one embodiment, the length is about 90 cm and the outside diameter is no more than about 0.110".

Tubular body 26 may be formed in any of a variety of manners which are well known in the art of catheter body manufacturing, such as by braiding and/or extrusion. Suitable extrudable materials include high density polyethylene, medium density polyethylene and other polyethylene blends, nylon, PEBAX, and others well known in the art. Reinforced tubular bodies may be produced by including a braided layer in or on the wall. The braided wall may comprise any of a variety of materials such as stainless steel, nitinol, composite fibers and others known in the art. Additional details concerning the tubular body 26 will be recited below.

The tubular body 26 is provided with a first guidewire lumen 28, extending axially therethrough between a proximal access port 30 and a distal access port 32. First lumen 28 preferably has an inside diameter of at least about 0.041" to accommodate a standard 0.035" diameter guidewire. Other inside diameters for first lumen 28 can readily be provided, based upon the desired guidewire diameter as is well understood in the art.

A second wire lumen 34 extends throughout at least a portion of the tubular body 26, between a proximal port 36 and a distal port 38. In an embodiment of the catheter 20 intended for implantation of a bifurcation prosthesis at the bifurcation of the abdominal aorta into the iliacs, the proximal access port 36 is positioned within the range of from about 40 cm to about 60 cm from the distal port 32. The distal port 38 is positioned within the range of from about 15 cm to about 20 cm from the distal port 32. The inside diameter of the second lumen 34 is configured to slideably receive a delivery system guidewire therethrough. In one embodiment, the inside diameter of the second lumen 34 is about 0.041", for use with a delivery system guidewire having an outside diameter of about 0.035".

In general, the axial distance between the proximal port 36 and the distal port 38 is sufficient to extend from a point outside of the body through an ipsilateral iliac puncture to about the bifurcation between the contralateral and ipsilateral iliacs. Thus, the length can vary depending upon the intended access site location along the femoral artery and the desired length of the dual lumen portion of the catheter which is to extend outside of the body.

The axial distance between proximal port 30 and proximal port 36 should be sufficient to extend from a point outside the contralateral femoral access site to the bifurcation. Typically, this length will be within the range from about 30 cm to about 40 cm, and usually at least about 35 cm.

The second lumen 34 is provided with a release or tear line 40, such as a crease, slot, series of perforations or other structure for facilitating easy opening or tearing of the side wall of the lumen 34, to permit the second wire extending through lumen 34 to be peeled laterally away from the catheter 20 as will be discussed. Alternatively, an axially extending slot may be provided in the radially outwardly facing wall of second lumen 34. Preferably, the two coaptive edges of the slot are biased into a closed position in contact or close proximity to each other under the resilience of the catheter body material. Thus, an axially extending slot which has a circumferential width of less than the diameter of the guidewire will retain the guidewire within the second lumen. However, the wall of the second lumen is sufficiently flexible that the guidewire may be peeled laterally through the slot by a plastic deformation thereof. Specific slot width and guidewire diameter relationships can be optimized through routine experimentation by one of skill in the art in view of the disclosure herein. In one embodiment, the tear line 40 is produced by an axially extending slot.

Dimensions of one particular embodiment of the present invention will be described in connection with FIGS. 1A through 1C. In this embodiment, the working length of the dual lumen catheter 20 is approximately 90±1.5 cm. The catheter body comprises a PEBAX extrusion, having a braided wire for reinforcing the first lumen 28. The braid filament comprises a round wire having a cross section of about 0.002". The proximal port 36 is spaced about 35.5 cm from the proximal luer connector. Port 36 has an axial length of about 1 cm, and is shaped as illustrated in FIG. 1C. The length of second lumen 34 between proximal port 36 and distal port 38 is about 35 cm. Distal port 38 has an axial length of about 1 cm, and the distal end of the catheter is about 17.5 cm beyond the distal edge of distal port 38. The diameter of the dual lumen catheter 20 at cross section 1B—1B is about 0.110". The inside diameter of the first lumen 28 is about 0.041", and the inside diameter of the second lumen 34 is about 0.039". Proximal and distal extensions of the second lumen 34 beyond the proximal port 36 and distal port 38 which are produced by the extrusion molding process as will be understood by those of skill in the art can be occluded such as by the introduction of a UV curable glue plug. At least the proximal plug adjacent proximal port 36 may be further provided with a radiopaque marker such as a gold marker to facilitate visualization during placement.

The foregoing dimensions and materials can be varied widely as will be appreciated by those of skill in the art in view of the desired performance characteristics and manufacturing techniques. In addition, the proximal port 36 and distal port 38 may be positioned elsewhere along the length of the catheter 20, as may be desired, to "reverse" the introduction method described in greater detail below. For example, although the discussion below relates to a design for a dual lumen catheter 20 intended for introduction into the contralateral iliac with a distal end exiting the ipsilateral iliac, the catheter 20 may also be adapted for introduction into the ipsilateral iliac as the primary access site. In this application, the catheter 20 is introduced into the ipsilateral iliac, advanced superiorly towards the aorta, and subsequently advanced inferiorly down the contralateral iliac and out the contralateral access site. The first and second wires are advanced distally through the catheter 20, one extending through a lateral exit port and into the abdominal aorta and the other exiting the contralateral iliac. The catheter 20 is thereafter proximally retracted from the ipsilateral iliac as will be apparent to those of skill in the art in view of the detailed description below, leaving the wires in place.

The method of using the dual lumen catheter 20 of the present invention will be described in connection with FIGS. 3 through 8. Referring to FIG. 3, there is disclosed a schematic representation of the abdominal part of the aorta and its principal branches. In particular, the abdominal aorta 42 is characterized by a right renal artery 44 and left renal artery 46. The large terminal branches of the aorta are the right and left common iliac arteries 48 and 50. Additional vessels (e.g. second lumbar, testicular, inferior mesenteric, middle sacral) have been omitted for simplification. An abdominal aortic aneurysm 52 is illustrated in the infrarenal portion of the diseased aorta.

A standard 0.035" diameter guidewire 54 is in position across the ipsilateral and contralateral iliacs 48 and 50. In accordance with the method of the present invention, the guidewire 54 is introduced from the contralateral side through a percutaneous puncture, and advanced superiorly towards the aorta 42. A retrieval catheter is introduced superiorly through a vascular access site and into the ipsilateral iliac, and used to grasp the guidewire 54 and retract it inferiorly and out through the ipsilateral vascular access site in accordance with known techniques.

Figure 5:
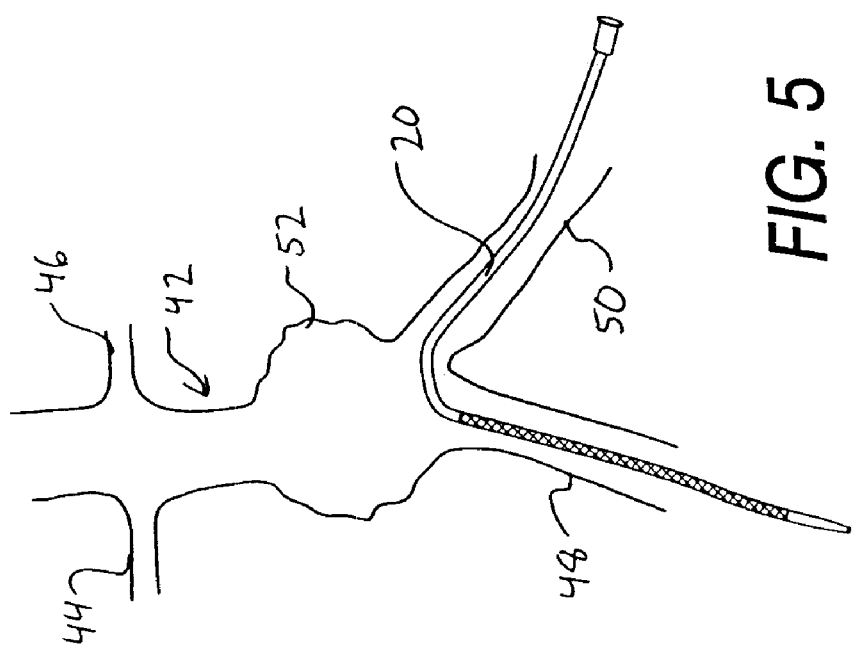
FIG. 5 is a schematic representation as in FIG. 4, after the guidewire has been removed from the dual lumen catheter.

Referring to FIG. 4, the dual lumen catheter 20 is advanced over the guidewire 54 from the contralateral access site along the guidewire 54 and out the ipsilateral access site. The guidewire is thereafter removed as seen in FIG. 5, leaving the dual lumen catheter 20 in position. The proximal end 22 of the dual lumen catheter 20 is positioned outside the patient on the contralateral iliac side, and the distal end 24 including the distal port 38 on second lumen 34 of dual lumen catheter 20 is positioned outside the patient on the ipsilateral iliac side.

Referring to FIG. 6, the delivery system guidewire 56 is introduced into the distal port 38 of the peel-away lumen 34. The delivery system guidewire 56 is advanced until the distal end 58 of the delivery system guidewire 56 extends out through proximal port 36 and across the aneurysm 52 into the aorta 42.

Figure 8:
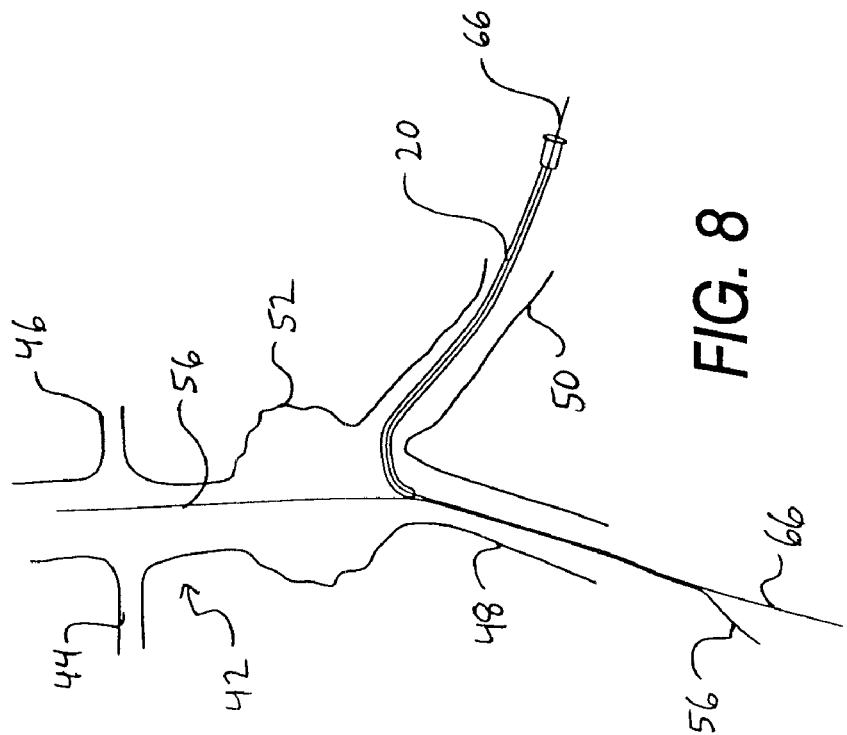
FIG. 8 is a schematic representation as in FIG. 7, with the dual lumen catheter in the process of being removed from the contralateral iliac, leaving both the delivery system guidewire and the contralateral deployment guidewire in position.
Figure 7:
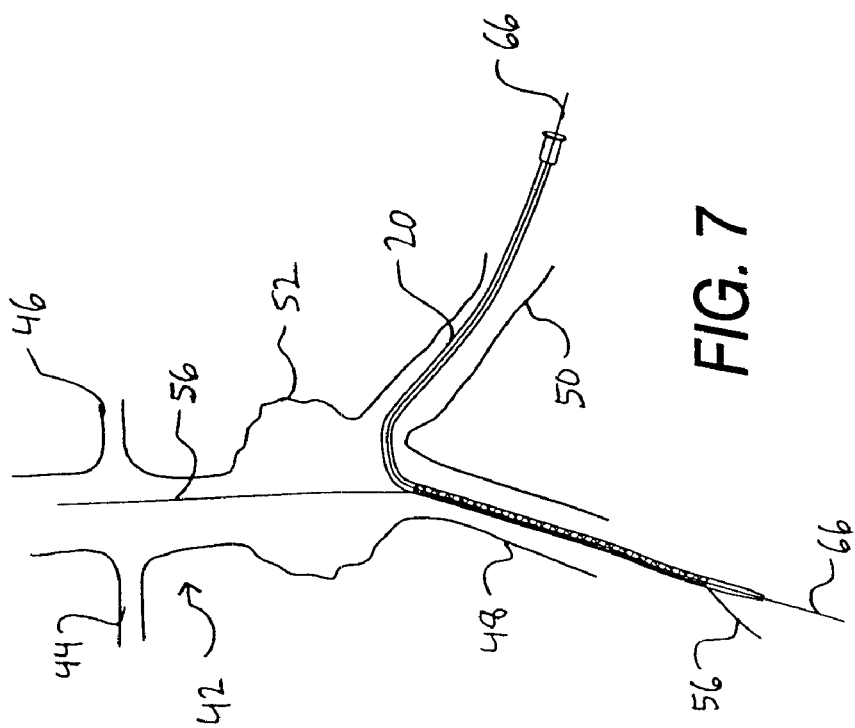
FIG. 7 is a schematic representation as in FIG. 6, with the contralateral branch deployment guidewire positioned within the dual lumen catheter.

The second procedure wire, typically a contralateral limb release wire 66, is introduced into and advanced throughout the first guidewire lumen 28. In a preferred application of the present invention, the wire 66 is the contralateral deployment wire, and is therefore introduced into the distal port 32 and advanced throughout the length of the first guidewire lumen 28 such that it exists the proximal port 30 on dual wire catheter 20. As shown in FIG. 8, the dual wire catheter 20 may thereafter be proximally retracted through the contralateral access site. The two wires 56 and 66 are manually retained in position such as by grasping the portions of the wires which extend from the ipsilateral access site. Proximal retraction of the dual wire catheter 20 from the contralateral access site causes the wire 56 to pull laterally through the wall of the second lumen 34 as has been discussed. In this manner, the dual wire catheter 20 may be removed from the body, leaving wires 56 and 66 in position.

Figure 9:
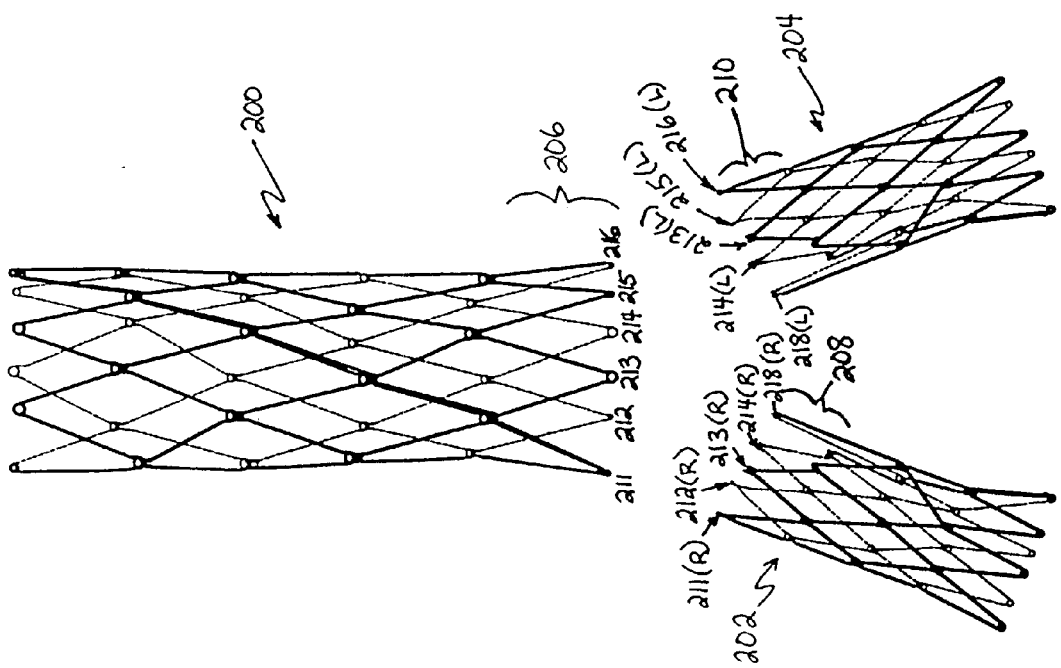
FIG. 9 is a schematic representation of an exemplary wire support structure for a bifurcated vascular prosthesis useful with the present invention, showing a main body support structure and separate branch support structures.

Referring to FIG. 9, there is disclosed an exploded schematic representation of a hinged or articulated tubular wire support structure for a bifurcated graft which may be deployed following placement of the procedure wires 56 and 66 discussed above. The tubular wire support comprises a main body, or aortic trunk portion 200 and right 202 and left 204 iliac branch portions. Right and left designations correspond to the anatomic designations of right and left common iliac arteries. The proximal end 206 of the aortic trunk portion 200 has apexes 211–216 adapted for connection with the complementary apexes on the distal ends 208 and 210 of the right 202 and left 204 iliac branch portions, respectively. Complementary pairing of apexes is indicated by the shared numbers, wherein the right branch portion apexes are designated by (R) and the left branch portion apexes are designated by (L). Each of the portions may be formed from a continuous single length of wire. See FIG. 11.

Figure 10:
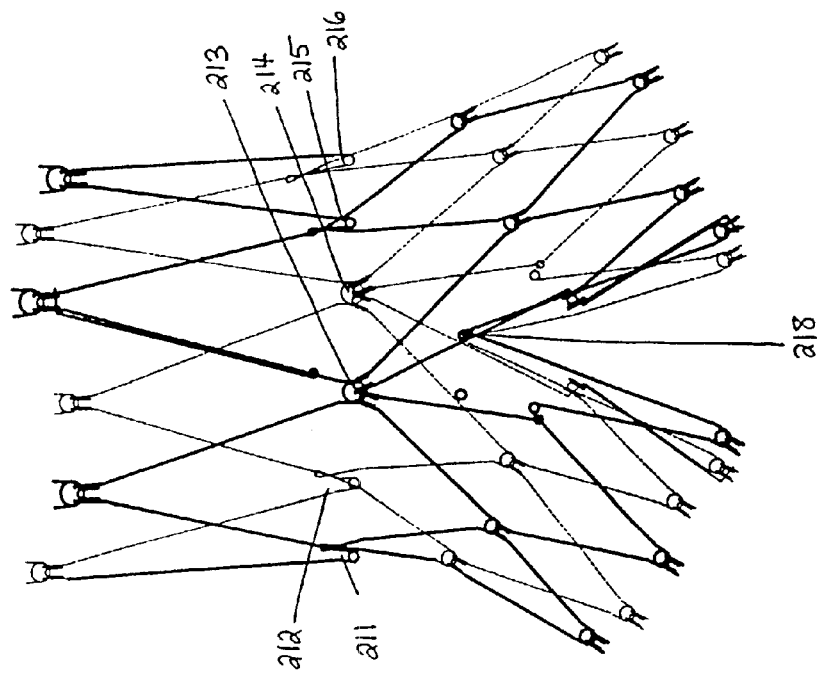
FIG. 10 is a schematic representation of the wire support structure as shown in FIG. 9, illustrating sliding articulation between the branch supports and the main body support.

Referring to FIG. 10, the assembled articulated wire support structure is shown. The central or medial apex 213 in the foreground (anterior) of the aortic trunk portion 200 is linked with 213(R) on the right iliac portion 202 and 213(L) on the left iliac portion 204. Similarly, the central apex 214 in the background (posterior) is linked with 214(R) on the right iliac portion 202 and 214(L) on the left iliac portion 204. Each of these linkages has two iliac apexes joined with one aortic branch apex. The linkage configurations may be of any of the variety described above in FIGS. 7A–D. The medial most apexes 218 (R) and (L) of the iliac branch portions 202 and 204 are linked together, without direct connection with the aortic truck portion 200.

The medial apexes 213 and 214 function as pivot points about which the right and left iliac branches 202, 204 can pivot to accommodate unique anatomies. Although the right and left iliac branches 202, 204 are illustrated at an angle of about 45° to each other, they are articulable through at least an angle of about 90° and preferably at least about 120°. The illustrated embodiment allows articulation through about 180° while maintaining patency of the central lumen. To further improve patency at high iliac angles, the apexes 213 and 214 can be displaced proximally from the transverse plane which roughly contains apexes 211, 212, 215 and 216 by a minor adjustment to the fixture about which the wire is formed. Advancing the pivot point proximally relative to the lateral apexes (e.g., 211, 216) opens the unbiased angle between the iliac branches 202 and 204.

In the illustrated embodiment, the pivot point is formed by a moveable link between an eye on apex 213 and two apexes 213R and 213L folded therethrough. To accommodate the two iliac apexes 213R and 213L, the diameter of the eye at apex 213 may be slightly larger than the diameter of the eye on other apexes throughout the graft. Thus, for example, the diameter of the eye at apex 213 in one embodiment made from 0.014" diameter wire is about 0.059", compared to a diameter of about 0.020" for eyes elsewhere in the graft.

Although the pivot points (apexes 213, 214) in the illustrated embodiment are on the medial plane, they may be moved laterally such as, for example, to the axis of each of the iliac branches. In this variation, each iliac branch will have an anterior and a posterior pivot link on or about its longitudinal axis, for a total of four unique pivot links at the bifurcation. Alternatively, the pivot points can be moved as far as to lateral apexes 211 and 216. Other variations will be apparent to those of skill in the art in view of the disclosure herein.

To facilitate lateral rotation of the iliac branches 202, 204 about the pivot points and away from the longitudinal axis of the aorta trunk portion 200 of the graft, the remaining links between the aorta trunk portion 200 and the iliac branches 202, 204 preferably permit axial compression and expansion. In general, at least one and preferably several links lateral to the pivot point in the illustrated embodiment permit axial compression or shortening of the graft to accommodate lateral pivoting of the iliac branch. If the pivot point is moved laterally from the longitudinal axis of the aorta portion of the graft, any links medial of the pivot point preferably permit axial elongation to accommodate lateral rotation of the branch. In this manner, the desired range of rotation of the iliac branches may be accomplished with minimal deformation of the wire, and with patency of the graft optimized throughout the angular range of motion.

To permit axial compression substantially without deformation of the wire, the lateral linkages, 211 and 212 for the right iliac, and 215 and 216 for the left iliac, may be different from the apex-to-apex linkage configurations illustrated elsewhere on the graft. The lateral linkages are preferably slideable linkages, wherein a loop formed at the distal end of the iliac apex slidably engages a strut of the corresponding aortic truck portion. The loop and strut orientation may be reversed, as will be apparent to those of skill in the art. Interlocking "elbows" without any distinct loop may also be used. Such an axially compressible linkage on the lateral margins of the assembled wire support structure allow the iliac branch portions much greater lateral flexibility, thereby facilitating placement in patients who often exhibit a variety of iliac branch asymmetries and different angles of divergence from the aortic trunk.

Referring to FIG. 11, there is illustrated a plan view of a single formed wire used for rolling about a longitudinal axis to produce a four segment straight tubular wire support for an iliac limb. The formed wire exhibits distinct segments, each corresponding to an individual tubular segment in the tubular supports 202 or 204 (See FIG. 9). The distal segment I, is adapted to articulate with the aortic trunk portion 200 and the adjacent iliac limb portion. The distal segment (I) has two apexes (e.g. corresponding to 211 and 212 on the right iliac portion 202 in FIG. 9) which form a loop adapted to slidably engage a strut in the lateral wall of the aortic portion. These articulating loops (A) are enlarged in FIG. 12A. As discussed above, the loops are preferably looped around a strut on the corresponding apex of the proximal aortic segment to provide a sliding linkage.

The apex 218 is proximally displaced relative to the other four apexes in the distal segment (I). Apex 218 (R or L) is designed to link with the complementary 218 apex on the other iliac branch portion (See FIG. 10). The apex 218 in the illustrated embodiment is formed adjacent or near an intersegment connector 66, which extends proximally from the distal segment.

The other apexes on the distal segment (I) of an iliac limb are designed to link with a loop on the corresponding apex of the proximal aortic segment. Because many variations of this linkage are consistent with the present invention (See U.S. patent application Ser. No. 09/251,363, filed Feb. 17, 1999, entitled Articulated Bifurcation Graft, the disclosure of which is incorporated in its entirety herein by reference), the form of the corresponding apexes may vary. In a preferred variation, the apexes (B) form a narrow U-shape, having an inside diameter of about 0.019" in an embodiment made from 0.012" Conichrome wire (tensile strength 300 ksi minimum) as illustrated in FIG. 12B. The U-shaped, elongated axial portion of the apex shown in FIG. 12B permits the apex to be wrapped through and around a corresponding loop apex of the proximal aortic segment.

In more general terms, the wire support illustrated in FIGS. 9 and 10 comprises a main body support structure formed from one or more lengths of wire and having a proximal end, a distal end and a central lumen extending along a longitudinal axis. The wire support also comprises a first branch support structure formed from one or more lengths of wire and having a proximal end, a distal end and a central lumen therethrough. The first branch support structure is pivotably connected to the proximal end of the main body support structure. The tubular wire support further comprises a second branch support structure formed from one or more lengths of wire and having a proximal end, a distal end and a central lumen extending therethrough. The distal end of the second branch support structure is pivotably connected to the proximal end of the main body support structure.

Further, the distal ends of the first and second branch structures may be joined together by a flexible linkage, formed for example between apexes 218(R) and 218(L) in FIG. 9. By incorporating a medial linkage between the two branch support structures and pivotable linkages with the main trunk, the first and second branch support structures can hinge laterally outward from the longitudinal axis without compromising the volume of the lumen. Thus, the branches may enjoy a wide range of lateral movement, thereby accommodating a variety of patient and vessel heterogeneity. Additional corresponding apexes between the main trunk and each iliac branch may also be connected, or may be free floating within the outer polymeric sleeve. Axially compressible lateral linkages, discussed above and illustrated in FIG. 10, may optionally be added.

The proximal apexes (C) of the iliac limb portions are adapted to link with the distal apexes of the next segment. These proximal apexes preferably form loops, such as those illustrated in FIG. 12C, wherein the elongated axial portions of the corresponding proximal apex in the adjacent segment can wrap around the loop, thereby providing flexibility of the graft.

The wire may be made from any of a variety of different alloys and wire diameters or non-round cross-sections, as has been discussed. In one embodiment of the bifurcation graft, the wire gauge remains substantially constant throughout the aorta component and steps down to a second, smaller cross-section throughout the iliac component.

A wire diameter of approximately 0.018" may be useful in the aorta trunk portion of a graft having five segments each having 2.0 cm length per segment, each segment having six struts intended for use in the aorta, while a smaller diameter such as 0.012" might be useful for segments of the graft having 6 struts per segment intended for the iliac artery.

In one embodiment of the present invention, the wire diameter may be tapered throughout from the proximal to distal ends of the aorta section and/or iliac section. Alternatively, the wire diameter may be tapered incremental or stepped down, or stepped up, depending on the radial strength requirements of each particular clinical application. In one embodiment, intended for the abdominal aortic artery, the wire has a cross-section of about 0.018" in the proximal zone and the wire tapers down regularly or in one or more steps to a diameter of about 0.012" in the distal zone of the graft. End point dimensions and rates of taper can be varied widely, within the spirit of the present invention, depending upon the desired clinical performance.

In general, in the tapered or stepped wire embodiments, the diameter of the wire in the iliac branches is no more than about 80% of the diameter of the wire in the aortic trunk. This permits increased flexibility of the graft in the region of the iliac branches, which has been determined by the present inventors to be clinically desirable.

The collapsed prosthesis in accordance with the present invention has a diameter in the range of about 2 to about 10 mm. Preferably, the maximum diameter of the collapsed prosthesis is in the range of about 3 to 6 mm (12 to 18 French). Some embodiments of the delivery catheter including the prosthesis will be in the range of from 18 to 20 or 21 French; other embodiments will be as low as 19F, 16F, 14F, or smaller. After deployment, the expanded endoluminal vascular prosthesis has radially self-expanded to a diameter anywhere in the range of about 20 to 40 mm, corresponding to expansion ratios of about 1:2 to 1:20. In a preferred embodiment, the expansion ratios range from about 1:4 to 1:8, more preferably from about 1:4 to 1:6.

The self expandable bifurcation graft of the present invention can be deployed at a treatment site in accordance with any of a variety of techniques as will be apparent to those of skill in the art. One such technique is disclosed in copending patent application Ser. No. 08/802,478 entitled Bifurcated Vascular Graft and Method and Apparatus for Deploying Same, filed Feb. 20, 1997, the disclosure of which is incorporated in its entirety herein by reference.

A partial cross-sectional side elevational view of one deployment apparatus 120 in accordance with the present invention is shown in FIG. 13. The deployment apparatus 120 comprises an elongate flexible multicomponent tubular body 122 having a proximal end 124 and a distal end 126. The tubular body 122 and other components of this system can be manufactured in accordance with any of a variety of techniques well known in the catheter manufacturing field. Suitable materials and dimensions can be readily selected taking into account the natural anatomical dimensions in the iliacs and aorta, together with the dimensions of the desired percutaneous access site.

The elongate flexible tubular body 122 comprises an outer sheath 128 which is axially movably positioned upon an intermediate tube 130. A central tubular core 132 is axially movably positioned within the intermediate tube 130. In one embodiment, the outer tubular sheath comprises extruded PTFE, having an outside diameter of about 0.250" and an inside diameter of about 0.230". The tubular sheath 128 is provided at its proximal end with a manifold 134, having a hemostatic valve 136 thereon and access ports such as for the infusion of drugs or contrast media as will be understood by those of skill in the art.

The outer tubular sheath 128 has an axial length within the range of from about 30" to about 40", and, in one embodiment of the deployment device 120 having an overall length of 105 cm, the axial length of the outer tubular sheath 128 is about 46 cm and the outside diameter is no more than about 0.250". Thus, the distal end of the tubular sheath 128 is located at least about 16 cm proximally of the distal end 126 of the deployment catheter 120 in stent loaded configuration.

As can be seen from FIGS. 14–16, proximal retraction of the outer sheath 128 with respect to the intermediate tube 130 will expose the compressed iliac branches of the graft, as will be discussed in more detail below.

A distal segment of the deployment catheter 120 comprises an outer tubular housing 138, which terminates distally in an elongate flexible tapered distal tip 140. The distal housing 138 and tip 140 are axially immovably connected to the central core 132 at a connection 142.

The distal tip 140 preferably tapers from an outside diameter of about 0.225" at its proximal end to an outside diameter of about 0.070" at the distal end thereof. The overall length of the distal tip 140 in one embodiment of the deployment catheter 120 is about 3". However, the length and rate of taper of the distal tip 140 can be varied depending upon the desired trackability and flexibility characteristics. The distal end of the housing 138 is secured to the proximal end of the distal tip 140 such as by thermal bonding, adhesive bonding, and/or any of a variety of other securing techniques known in the art. The proximal end of distal tip 140 is preferably also directly or indirectly connected to the central core 132 such as by a friction fit and/or adhesive bonding.

In at least the distal section of the catheter, the central core 132 preferably comprises a length of hypodermic needle tubing. The hypodermic needle tubing may extend throughout the length catheter to the proximal end thereof, or may be secured to the distal end of a proximal extrusion as illustrated for example in FIG. 22. A central guidewire lumen 144 extends throughout the length of the tubular central core 132, having a distal exit port 146 and a proximal access port 148 as will be understood by those of skill in the art.

Referring to FIGS. 14–16, a bifurcated endoluminal graft 150 is illustrated in a compressed configuration within the deployment catheter 120. The graft 150 comprises a distal aortic section 152, a proximal ipsilateral iliac portion 154, and a proximal contralateral iliac portion 156. The aortic trunk portion 152 of the graft 150 is contained within the tubular housing 138. Distal axial advancement of the central tubular core 132 will cause the distal tip 140 and housing 138 to advance distally with respect to the graft 150, thereby permitting the aortic trunk portion 152 of the graft 150 to expand to its larger, unconstrained diameter. Distal travel of the graft 150 is prevented by a distal stop 158 which is axially immovably connected to the intermediate tube 130. Distal stop 158 may comprise any of a variety of structures, such as an annular flange or component which is adhered to, bonded to or integrally formed with a tubular extension 160 of the intermediate tube 132. Tubular extension 160 is axially movably positioned over the hypotube central core 132.

The tubular extension 160 extends axially throughout the length of the graft 150. At the proximal end of the graft 150, a step 159 axially immovably connects the tubular extension 160 to the intermediate tube 130. In addition, the step 159 provides a proximal stop surface to prevent proximal travel of the graft 150 on the catheter 120. The function of step 159 can be accomplished through any of a variety of structures as will be apparent to those of skill in the art in view of the disclosure herein. For example, the step 159 may comprise an annular ring or spacer which receives the tubular extension 160 at a central aperture therethrough, and fits within the distal end of the intermediate tube 130. Alternatively, the intermediate tube 130 can be reduced in diameter through a generally conical section or shoulder to the diameter of tubular extension 160.

Proximal retraction of the outer sheath 128 will release the iliac branches 154 and 156 of the graft 150. The iliac branches 154 and 156 will remain compressed, within a first (ipsilateral) tubular sheath 162 and a second (contralateral) tubular sheath 164. The first tubular sheath 162 is configured to restrain the ipsilateral branch of the graft 150 in the constrained configuration, for implantation at the treatment site. The first tubular sheath 162 is adapted to be axially proximally removed from the iliac branch, thereby permitting the branch to expand to its implanted configuration. In one embodiment, the first tubular sheath 162 comprises a thin walled PTFE extrusion having an outside diameter of about 0.215" and an axial length of about 7.5 cm. A proximal end of the tubular sheath 162 is necked down such as by heat shrinking to secure the first tubular sheath 162 to the tubular extension 160. In this manner, proximal withdrawal of the intermediate tube 130 will in turn proximally advance the first tubular sheath 162 relative to the graft 150, thereby deploying the self expandable iliac branch of the graft 150.

The second tubular sheath 164 is secured to the contralateral guidewire 166 (equivalent to guidewire 66 discussed previously), which extends outside of the tubular body 122 at a point 168, such as may be conveniently provided at the junction between the outer tubular sheath 128 and the distal housing 138. The second tubular sheath 164 is adapted to restrain the contralateral branch of the graft 150 in the reduced profile. In one embodiment of the invention, the second tubular sheath 164 has an outside diameter of about 0.215" and an axial length of about 7.5 cm. The second tubular sheath 164 can have a significantly smaller cross-section than the first tubular sheath 162, due to the presence of the tubular core 132 and intermediate tube 130 within the first iliac branch 154.

The second tubular sheath 164 is secured at its proximal end to a distal end of the contralateral guidewire 166. This may be accomplished through any of a variety of securing techniques, such as heat shrinking, adhesives, mechanical interfit and the like. In one embodiment, the guidewire is provided with a knot or other diameter enlarging structure to provide an interference fit with the proximal end of the second tubular sheath 156, and the proximal end of the second tubular sheath 156 is heat shrunk and/or bonded in the area of the knot to provide a secure connection. Any of a variety of other techniques for providing a secure connection between the contralateral guidewire 166 and tubular sheath 156 can readily be used in the context of the present invention as will be apparent to those of skill in the art in view of the disclosure herein. The contralateral guidewire 166 can comprise any of a variety of structures, including polymeric monofilament materials, braided or woven materials, metal ribbon or wire, or conventional guidewires as are well known in the art.

In use, the free end of the contralateral guidewire 166 is advanced through the first lumen 28 of a dual lumen catheter 20 as has been discussed.

Figure 17:
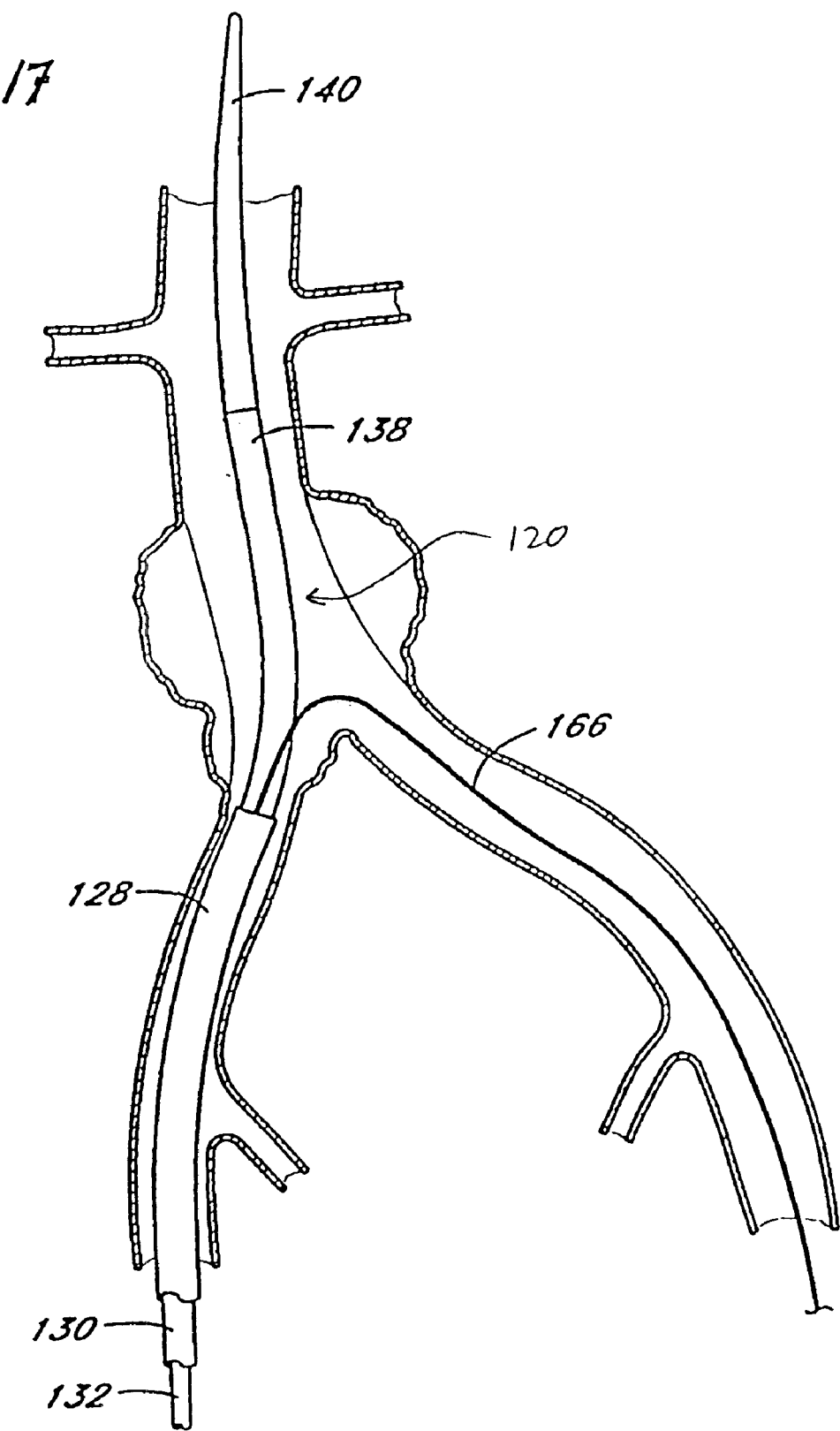
FIG. 17 is a schematic representation of a bifurcated graft deployment catheter positioned within the ipsilateral iliac and the aorta, with the contralateral guidewire positioned within the contralateral iliac.
Figure 18:
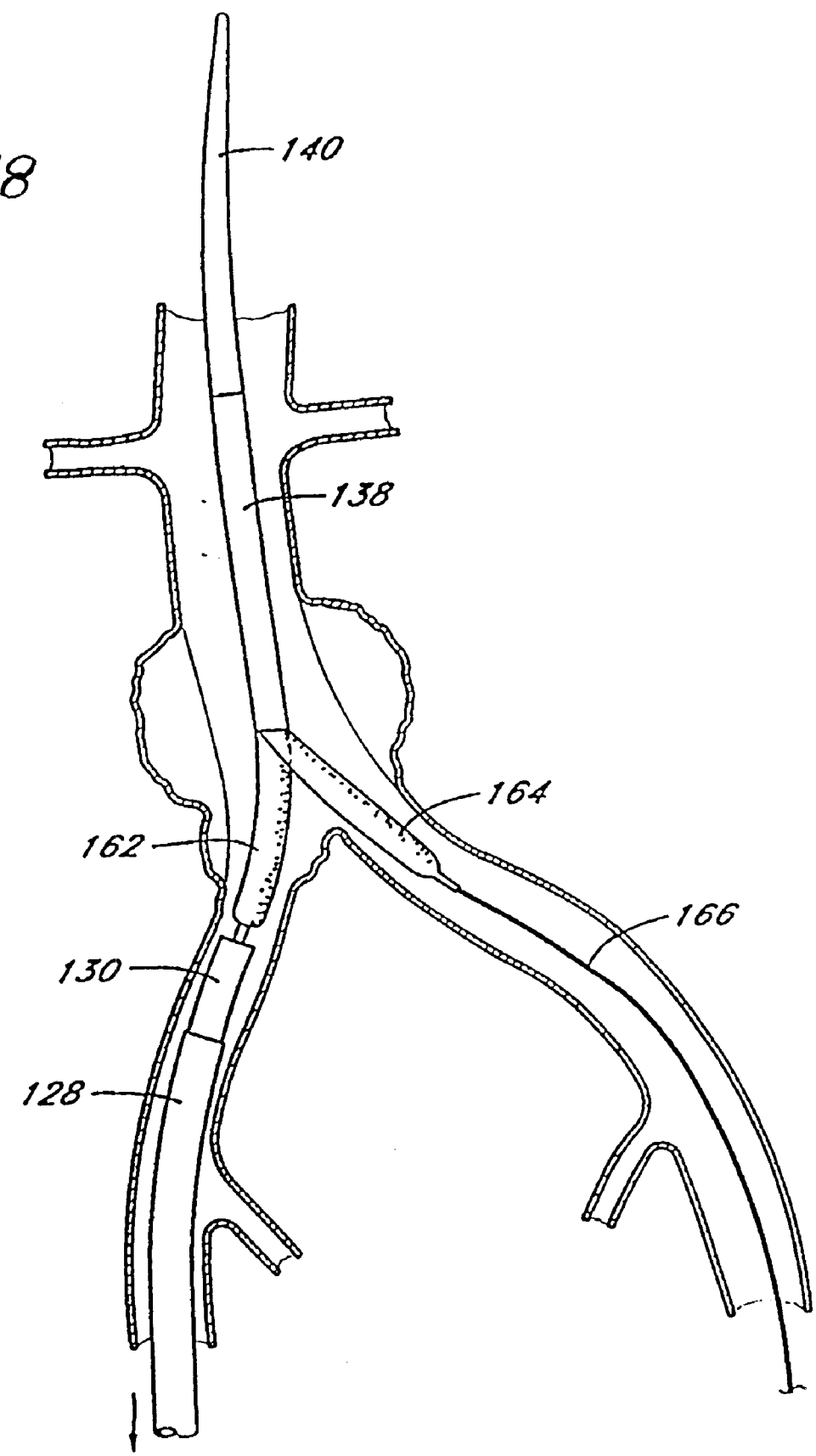
FIG. 18 is a schematic representation as in FIG. 17, with the outer sheath proximally retracted and the compressed iliac branches of the graft moving into position within the iliac arteries.

The deployment catheter 120 is thereafter percutaneously inserted into the first puncture, and advanced along guidewire 56 (e.g. 0.035 inch) through the ipsilateral iliac and into the aorta. As the deployment catheter 120 is transluminally advanced, slack produced in the contralateral guidewire 166 is taken up by proximally withdrawing the guidewire 166 from the second percutaneous access site. In this manner, the deployment catheter 120 is positioned in the manner generally illustrated in FIG. 17. Referring to FIG. 18, the outer sheath 128 is proximally withdrawn while maintaining the axial position of the overall deployment catheter 120, thereby releasing the first and second iliac branches of the graft 150. Proximal advancement of the deployment catheter 120 and contralateral guidewire 166 can then be accomplished, to position the iliac branches of the graft 150 within the iliac arteries as illustrated.

Figure 19:
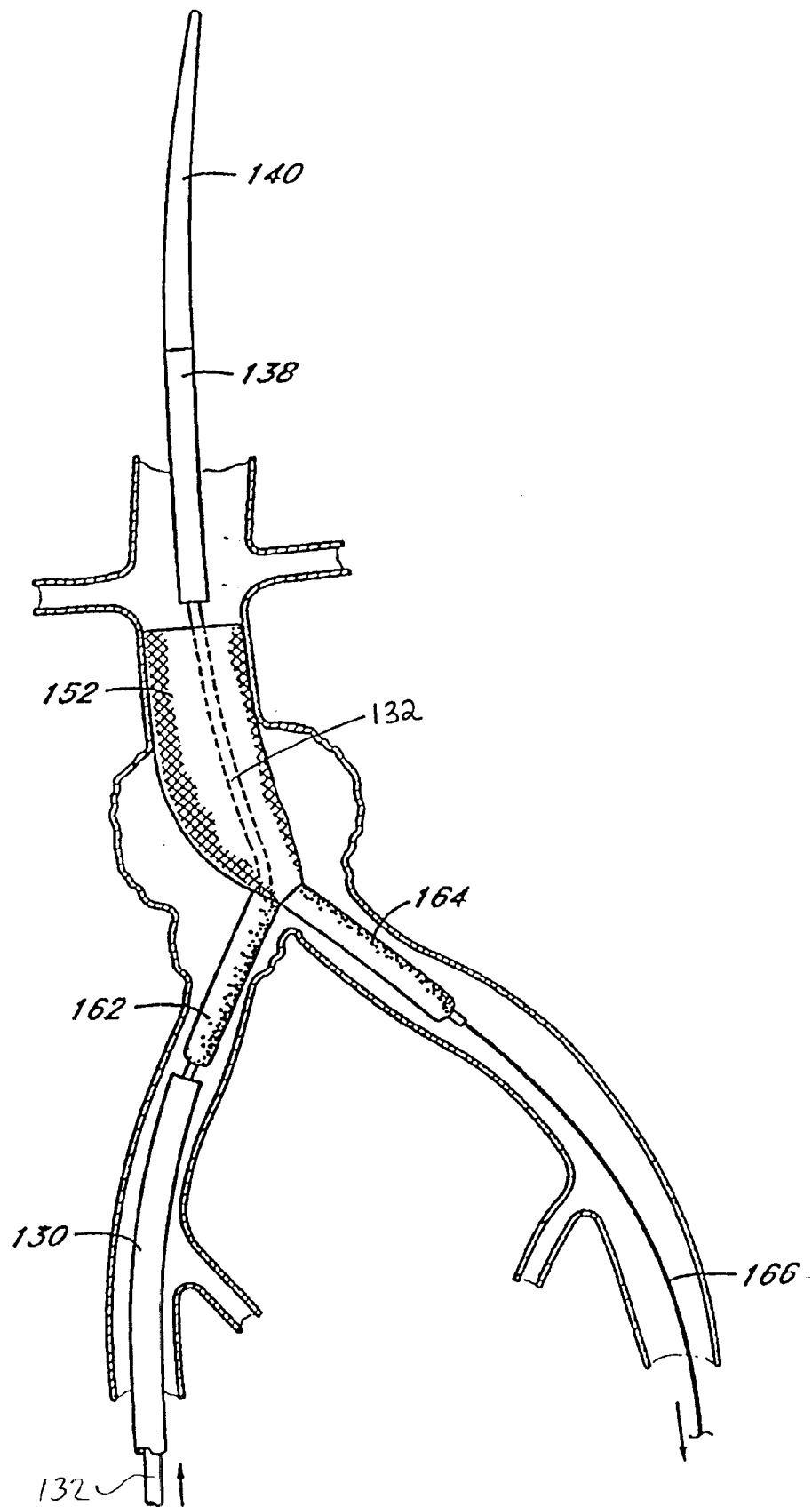
FIG. 19 is a schematic representation as in FIG. 18, with the compressed iliac branches of the graft within the iliac arteries, and the main aortic trunk of the graft deployed within the aorta.
Figure 20:
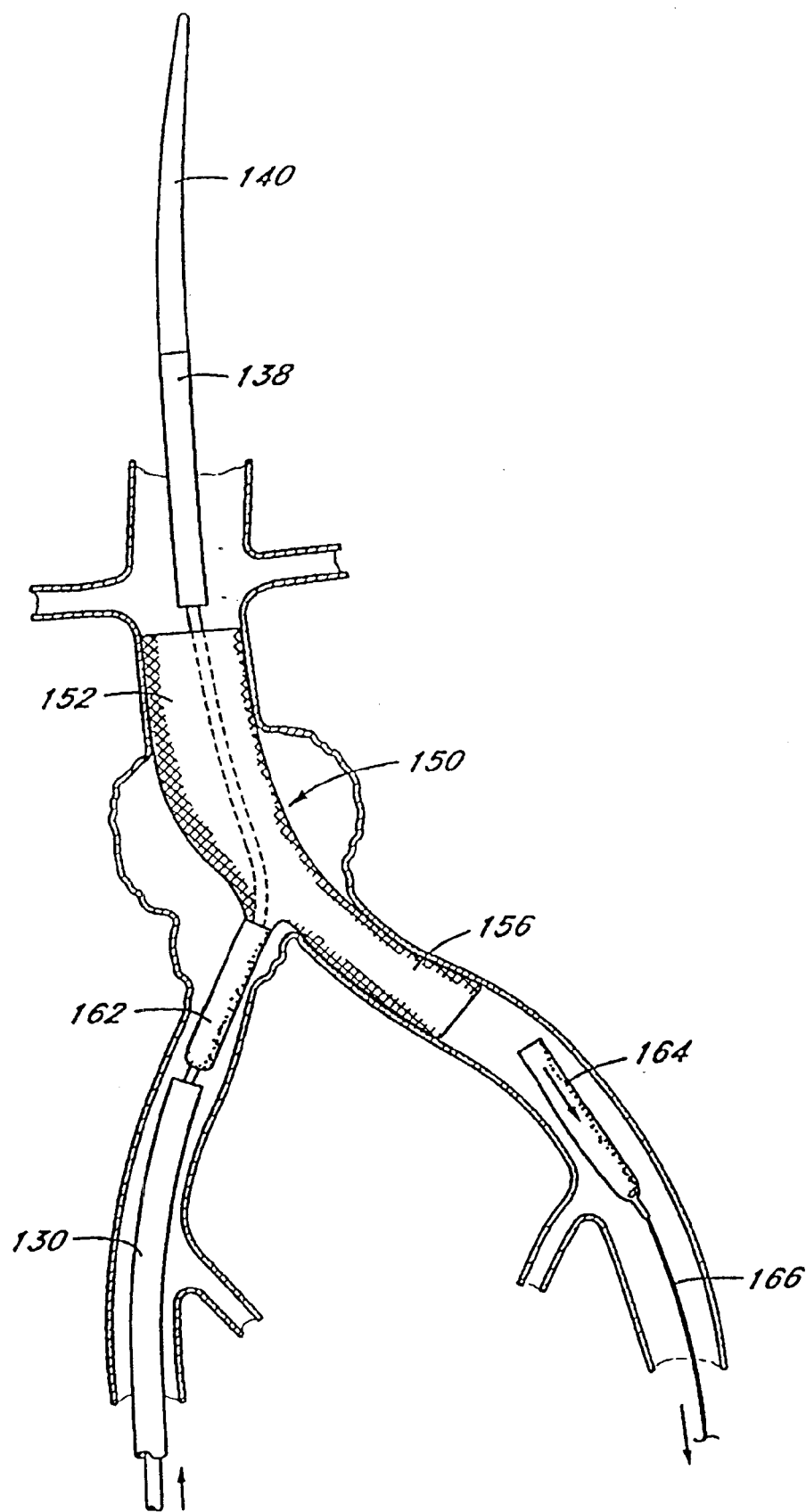
FIG. 20 is a schematic representation as in FIG. 19, with the contralateral iliac branch of the graft deployed.

Referring to FIG. 19, the central core 132 is distally advanced thereby distally advancing the distal housing 138. This exposes the aortic trunk 152 of the graft 150, which deploys into its fully expanded configuration within the aorta. As illustrated in FIG. 20, the contralateral guidewire 166 is thereafter proximally withdrawn, thereby by proximally withdrawing the second sheath 164 from the contralateral iliac branch 156 of the graft 150. The contralateral branch 156 of the graft 150 thereafter self expands to fit within the iliac artery. The guidewire 166 and sheath 164 may thereafter be proximally withdrawn and removed from the patient, by way of the second percutaneous access site.

Figure 21:
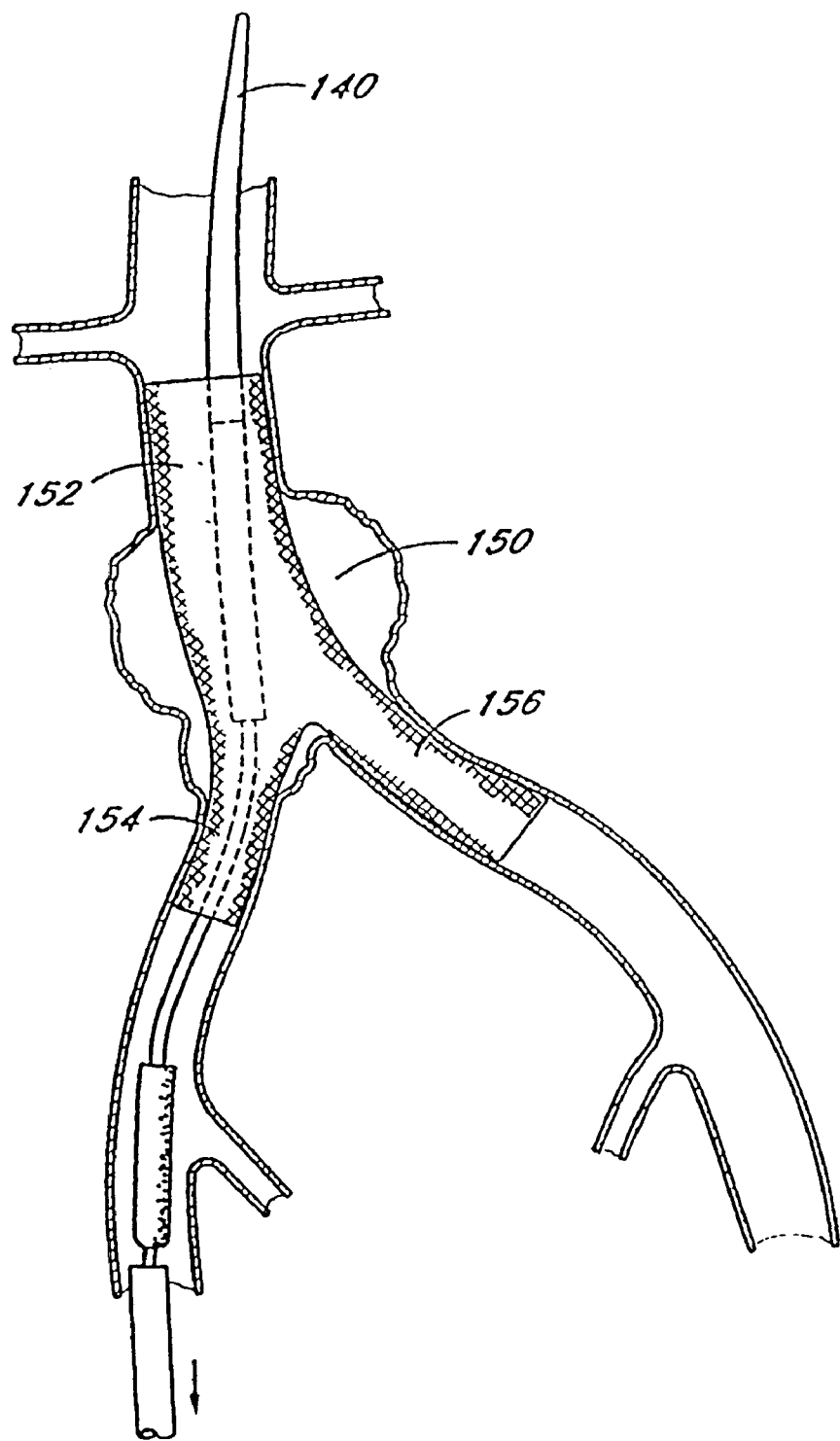
FIG. 21 is a schematic representation as in FIG. 20, following deployment of the ipsilateral branch of the graft.

Thereafter, the deployment catheter 120 may be proximally withdrawn to release the ipsilateral branch 154 of the graft 150 from the first tubular sheath 162 as shown in FIG. 21. Following deployment of the ipsilateral branch 154 of the prosthesis 150, a central lumen through the aortic trunk 152 and ipsilateral branch 154 is sufficiently large to permit proximal retraction of the deployment catheter 120 through the deployed bifurcated graft 150. The deployment catheter 120 may thereafter be proximally withdrawn from the patient by way of the first percutaneous access site.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

What is claimed is:

1. A method of positioning a first wire through a portion of a first branch vessel, across a bifurcation of a main vessel and through a portion of a second branch vessel, and a second wire through the portion of the first branch vessel and into the main vessel, comprising the steps of:
   introducing a catheter through a first access site and into the first branch vessel, the catheter having at least first and second lumens;
   advancing the catheter superiorly to the bifurcation of the main vessel and inferiorly down the second branch vessel to a second access site;
   introducing a first wire through the first lumen and between the first access site and the second access site;
   introducing a second wire through the second lumen superiorly through the first branch vessel and into the main vessel; and
   removing the catheter, while leaving the first and second wires in place.

2. A method as in claim 1, wherein the removing step comprises tearing the wall of the second lumen in response to proximal retraction of the catheter.

3. A method as in claim 1, wherein the advancing the catheter step comprises advancing the catheter along a third wire.

4. A method as in claim 1, wherein the first wire comprises a release wire for releasing a second branch vessel portion of a bifurcation graft from a constrained configuration to an expanded configuration.

5. A method as in claim 1, further comprising the step of introducing a bifurcation graft delivery catheter into the main vessel along the second wire.

6. The method as in claim 3, wherein the third wire is percutaneously introduced into one of the first branch vessel and the second branch vessel prior to the advancing the catheter step.

7. The method as in claim 3, wherein further comprising the step of removing the third wire prior to the step of introducing the first wire.

8. The method as in claim 3, wherein the second lumen has a proximal opening and a distal opening, and the introducing a catheter step comprises introducing the catheter to a position in which the proximal opening is positioned in between the first access site and the second access site.

9. The method as in claim 8, wherein the proximal opening is positioned at the bifurcation.

10. A method of positioning a first wire through a portion of a first branch vessel that branches from a main vessel, across a branching of the main vessel and through a portion of a second branch vessel, and a second wire through the portion of the first branch vessel and into the main vessel, comprising the steps of:
   introducing a catheter through a first access site and into the first branch vessel, the catheter having at least first and second lumens;
   advancing the catheter superiorly to the bifurcation of the main vessel and inferiorly down the second branch vessel to a second access site;
   introducing a first wire through the first lumen and between the first access site and the second access site;

introducing a second wire through the second lumen superiorly through the first branch vessel and into the main vessel; and removing the catheter, while leaving the first and second wires in place.

11. A method as in claim 10, wherein the removing step comprises tearing the wall of the second lumen in response to proximal retraction of the catheter.

12. A method as in claim 10, wherein the first wire comprises a release wire for releasing a second branch vessel portion of a bifurcation graft from a constrained configuration to an expanded configuration.

13. A method as in claim 10, wherein the advancing the catheter step comprises advancing the catheter along a third wire.

14. The method as in claim 13, wherein the third wire is percutaneously introduced into one of the first branch vessel and the second branch vessel prior to the advancing the catheter step.

15. The method as in claim 13, wherein further comprising the step of removing the third wire prior to the step of introducing the first wire.

16. The method as in claim 10, wherein the second lumen has a proximal opening and a distal opening, and the introducing a catheter step comprises introducing the catheter to a position in which the proximal opening is positioned in between the first access site and the second access site.

17. The method as in claim 16, wherein the proximal opening is positioned at the bifurcation.

18. A method of transluminally deploying a bifurcation graft at the bifurcation of a main vessel into a first branch vessel and a second branch vessel; comprising the steps of:

introducing a catheter through a first access site and into the first branch vessel, the catheter having at least first and second lumens;

advancing the catheter superiorly to the bifurcation of the main vessel and inferiorly down the second branch vessel to a second access site;

introducing a first wire through the first lumen from the first access site through the second access site;

introducing a second wire through the second lumen from the first access site superiorly through the first branch vessel and into the aorta;

removing the catheter, while leaving the first and second wires in place; and deploying a bifurcation graft at the bifurcation of the main vessel into the first and second branch vessels.

19. A method as in claim 18, wherein the removing step comprises tearing the wall of the second lumen in response to proximal retraction of the catheter.

20. A method as in claim 18, wherein the advancing the catheter step comprises advancing the catheter along a third wire.

21. A method as in claim 18, wherein the first wire comprises a release wire for releasing a second vessel branch portion of a bifurcation graft from a constrained configuration to an expanded configuration.

22. A method as in claim 18, further comprising the step of introducing a bifurcation graft delivery catheter into the main vessel along the second wire.

23. The method as in claim 18, wherein the second lumen has a proximal opening and a distal opening, and the introducing a catheter step comprises introducing the catheter to a position in which the proximal opening is positioned in between the first access site and the second access site.

24. The method as in claim 23, wherein the proximal opening is positioned at the bifurcation.

25. The method as in claim 20, wherein the third wire is percutaneously introduced into one of the first branch vessel and the second branch vessel prior to the advancing the catheter step.

26. The method as in claim 20, wherein further comprising the step of removing the third wire prior to the step of introducing the first wire.

27. The method as in claim 18, wherein the deploying step comprises deploying a self expanding bifurcation graft.

* * * * *